US011446248B2

(12) United States Patent
Seneci

(10) Patent No.: US 11,446,248 B2
(45) Date of Patent: Sep. 20, 2022

(54) PROCESS FOR THE PREPARATION OF DELAYED RELEASE SOLID FORMULATIONS

(71) Applicant: GRAAL S.r.l., Monza (IT)

(72) Inventor: Antonio Enrico Seneci, Monza (IT)

( * ) Notice: Subject to any disclaimer, the term of this patent is extended or adjusted under 35 U.S.C. 154(b) by 0 days.

(21) Appl. No.: 16/957,972

(22) PCT Filed: Dec. 21, 2018

(86) PCT No.: PCT/IB2018/060501
§ 371 (c)(1),
(2) Date: Jun. 25, 2020

(87) PCT Pub. No.: WO2019/130193
PCT Pub. Date: Jul. 4, 2019

(65) Prior Publication Data
US 2020/0345644 A1    Nov. 5, 2020

(30) Foreign Application Priority Data

Dec. 27, 2017   (IT) .......................... 102017000149917

(51) Int. Cl.
*A61K 9/16*   (2006.01)
*A61K 9/50*   (2006.01)
*A61K 9/00*   (2006.01)
*A61K 45/06*   (2006.01)

(52) U.S. Cl.
CPC .......... *A61K 9/1694* (2013.01); *A61K 9/1617* (2013.01); *A61K 9/0053* (2013.01); *A61K 45/06* (2013.01)

(58) Field of Classification Search
None
See application file for complete search history.

(56) References Cited

U.S. PATENT DOCUMENTS

| 5,422,121 A * | 6/1995 | Lehmann | ............. A61K 9/1635 424/464 |
| 6,194,005 B1 * | 2/2001 | Farah | ................... A61K 9/1617 424/468 |
| 2010/0151095 A1 * | 6/2010 | Besse | .................... A23G 1/201 426/303 |
| 2011/0250286 A1 * | 10/2011 | Marcello | ................ A61K 47/12 424/498 |

FOREIGN PATENT DOCUMENTS

| EP | 0935459 B1 | 6/2002 |
| EP | 1225876 B1 | 2/2004 |
| EP | 1985188 B1 | 2/2013 |
| WO | WO-2011127236 A1 | 10/2011 |

* cited by examiner

*Primary Examiner* — Brian Gulledge
(74) *Attorney, Agent, or Firm* — Scott D. Swanson; Shaver & Swanson, LLP

(57) ABSTRACT

A process for the preparation of oral delayed release solid formulations and the formulations obtainable from said process are now described. Said process comprises the following steps: a) melting at least one lipid; b) spraying said at least one melted lipid on at least one active ingredient in the form of a moving powder; c) cooling the resulting mixture; d) optional granulation of the mixture; e) optional compression of the mixture.

18 Claims, 3 Drawing Sheets

Lipid transfer and spraying equipment

Figure 1. Lipid transfer and spraying equipment

Figure 2. Lipid delivery cylinder

Figure 3. Homogeneity of the MgO mixture obtained according to EP1225876
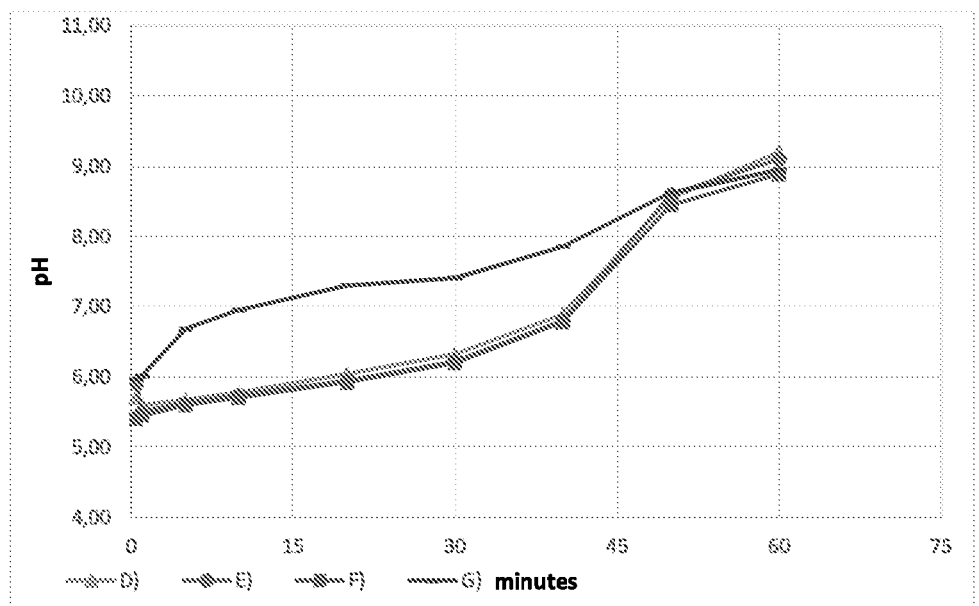
Figure 4. Homogeneity of the MgO mixture obtained according to the present invention
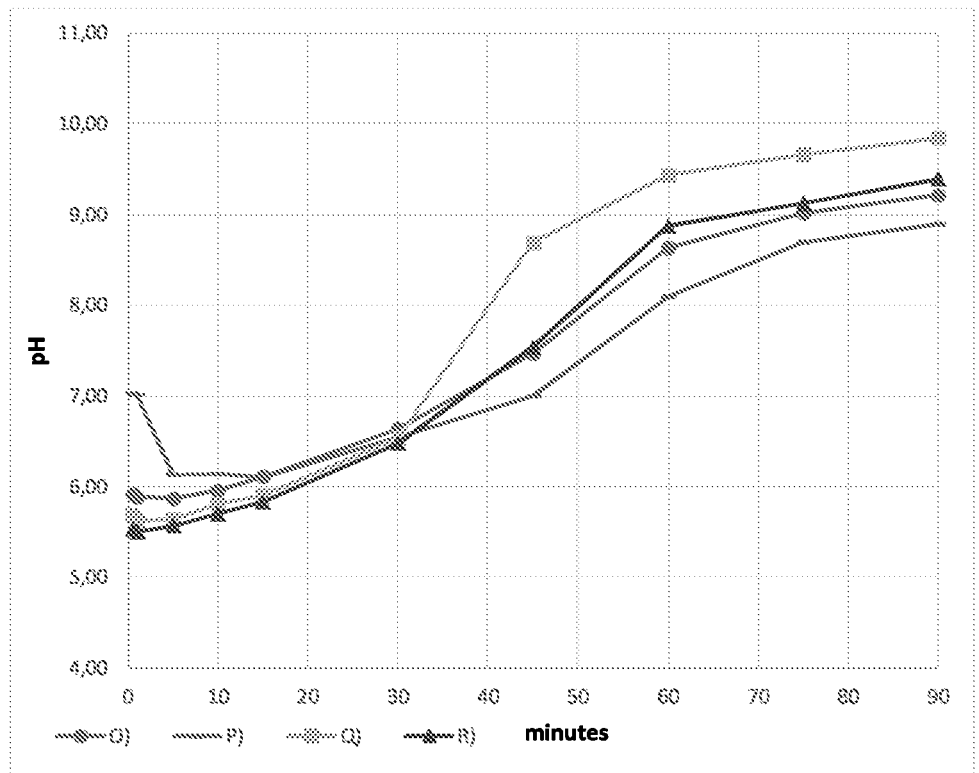

Figure 5. Dissolution of the MgO granulate obtained according to EP1225876 (I) vs MgO granulate according to the present invention (H)
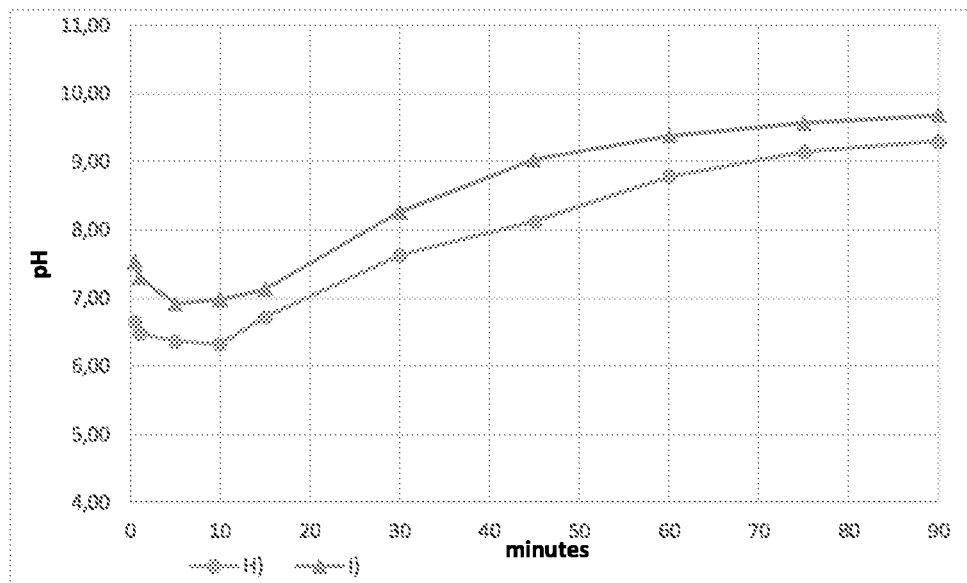
Figure 6. Dissolution of potassium citrate monohydrate tablets obtained according to EP1225876 (A) vs K tablets according to the present invention (B).
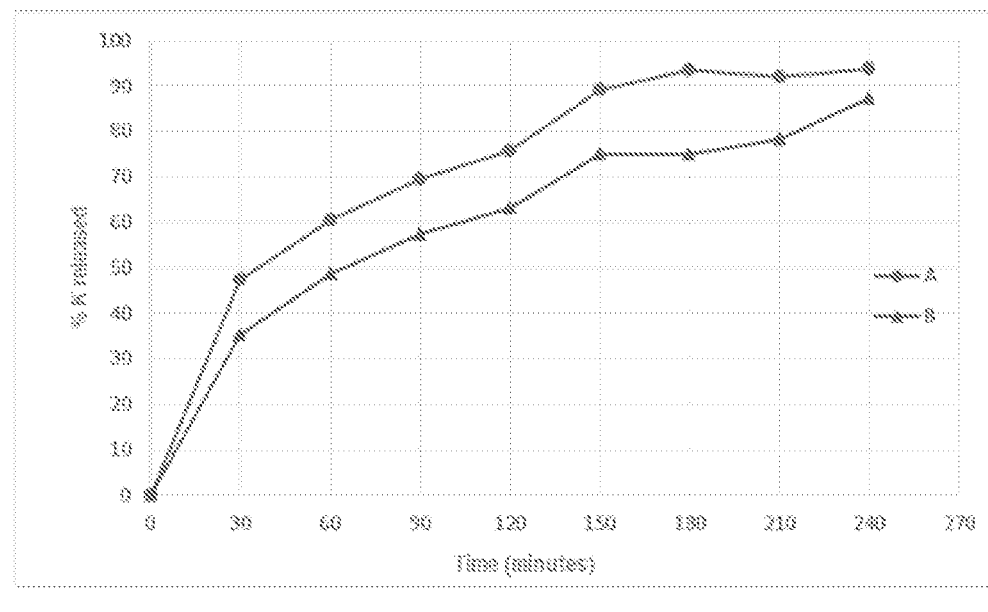
Time (minutes)

PROCESS FOR THE PREPARATION OF DELAYED RELEASE SOLID FORMULATIONS

The object of the present invention is a process for the preparation of oral delayed release solid formulations and the formulations obtainable from said process.

STATE OF THE ART

"Delayed release preparations" are solid consistency formulations, administered orally, which are prepared using special techniques, thanks to which the active ingredient(s) are always gradually absorbed at the intestinal level. In some cases, depending on the needs of administration, the delayed-release preparations may alternatively release a portion of the active ingredient at the stomach level and the remaining portion in the intestine, or these preparations may allow the active ingredient to be gradually released only at the intestinal level.

The main methodologies, currently applied in the prior art, for the preparation of delayed release formulations allow to obtain the following solid formulations:

A) Film-coated tablets, with coatings commonly made of plant-derived polymeric substances, such as ethyl cellulose, cellulose acetophthalate, polyacrylates, shellac, keratin, and other polymeric substances capable of isolating the coated substances from the enzyme digestive action, and therefore delay their intestinal absorption. This coating operation is usually performed in isolated rooms, using special equipment generally consisting of coating pans or fluidized bed nebulizer systems, which require sophisticated systems for spraying the coating solution, considerable amounts of air for drying, and adequate filtration systems and/or abatement of various substances, dispersed by hot air during drying, to work properly.

B) Tablets whose composition include chronoids consisting of active ingredients coated with film-forming solutions, similar to those described at point A), capable of delaying their absorption. The slow release chronoids present in the tablets can in turn be dispersed and mixed with diluents in which some of the substances being coated may also be present.

C) Capsule shells also containing chronoids consisting of the active ingredients coated with film-forming solutions, similar to those already described at point A), capable of delaying their absorption.

D) Delayed release gastroresistant tablets, like those described in EP1225876, consisting of a tablet formulation in which the active ingredients, mixed with particular lipophilic natural substances, biocompatible with the body's digestive processes, are present. These lipophilic substances, mixed with the active ingredients, form a delayed release preparation, which allows body's absorption of active ingredients to be modified by exploiting the physiological digestive process which is usually slowed down by the presence of fats or lipophilic substances in the gastro-intestinal tract.

The lipophilic substances described in EP1225876 are able to delay absorption of the active ingredients and can be added by melting or direct mixing to the active ingredients subjected to delayed release treatment. The percentage of lipophilic substances used to obtain this modified release condition is usually of between 5% and 30%, with respect to the weight of the formulation containing the active ingredient.

However, the method described above, based on a lipid and active ingredient random mixing process, has the disadvantage of having a non-homogeneous and random distribution of the lipid on the surface of the mixture, and requires a greater amount of lipids to increase the probability of a full and more homogeneous coating of the mixture.

There is therefore a need to develop a process for the preparation of delayed release oral formulations that allows to more accurately control the different steps of lipid addition, distribution, and mixing, in order to have a more uniform distribution of the lipid on the mixture and, at the same conditions of extended release, limit the amount of lipophilic substances used to reduce the lipid load in the final formulation.

Definitions

Unless otherwise defined, all terms of the art, notations, and other scientific terms used herein are intended to have the meanings commonly understood by those skilled in the art to which this description belongs. In some cases, terms with meanings that are commonly understood are defined herein for clarity and/or ready reference; therefore, the inclusion of such definitions herein should not be construed as being representative of a substantial difference with respect to what is generally understood in the art.

The terms "comprising", "having", "including", and "containing" are to be construed as open-ended terms (i.e., meaning "comprising, but not limited to"), and are to be considered as a support also for terms such as "consist essentially of", "consisting essentially of", or "consisting of".

The terms "consists essentially of", "consisting essentially of" are to be construed as semi-closed terms, meaning that no other ingredients which materially affects the novel characteristics of the invention are included (optional excipients may therefore be included).

The terms "consists of", "consisting of" are to be construed as closed terms. The term "physiologically acceptable excipient" refers to a substance devoid of any pharmacological effects of its own, and that does not produce adverse reactions when administered to a mammal, preferably a human being. Physiologically acceptable excipients are well known in the art and are described, for example, in Handbook of Pharmaceutical Excipients, sixth edition 2009, incorporated herein by reference.

The term "delayed release formulation or composition" refers to a form of administration that allows the active ingredient(s) contained therein to be released after a predetermined time period.

The term "lipid" comprises both triglycerides and fatty acids, and mixtures thereof.

The term "gastro-resistant coating" refers to a coating that allows the composition to pass through the gastric tract without being damaged and then release the active ingredient(s) into the intestine.

The term "moving powder" means the advancement of the powder in the direction of the perpendicular line formed by the nozzles and the bed of the same powder, as shown in FIGS. 1 and 2.

The term "spraying" means the dripping of melted lipid without the use of compressed air, i.e. at a pressure of less than 3 bar, preferably of between 0.5 and 1.5 bar.

DRAWINGS

FIG. 1: equipment for transferring and spraying the lipid, with the dispensing cylinder placed horizontally on the kneader and the nozzles arranged linearly in an ordered sequence, along the circular section thereof.

FIG. 2: lipid dispensing cylinder in which the nozzles inclination angle of 45°, with respect to the active ingredient powder advancement plan, is shown.

FIG. 3. Homogeneity of the MgO-based mixture samples obtained by simple mixing according to the method described in EP1225876

FIG. 4. Homogeneity of the MgO-based mixture samples according to the process of the present invention FIG. 5. Comparison between the dissolution of an MgO-based granulate obtained by simple mixing according to the method described in EP1225876 (I) and an MgO-based granulate having identical qualitative-quantitative composition but obtained according to the process of the present invention (H)

FIG. 6. Comparison between the dissolution of a potassium citrate monohydrate-based granulate obtained by simple mixing according to the method described in EP1225876 and a potassium citrate monohydrate-based granulate having the same qualitative-quantitative composition but obtained according to the process of the present invention.

DESCRIPTION OF THE INVENTION

It was surprisingly observed that by applying a new and particular industrial process, which involves spraying a melted lipid on the active ingredient in the form of a powder under stirring, it is possible to obtain delayed release solid formulations having improved properties with respect to formulations known in the art, such as those described in EP1225876.

In particular, the new process according to the present invention allows to obtain a more homogeneous and reproducible dispersion of the active ingredient within the lipophilic mass, with a resulting more uniform and controlled release of the same active ingredient; this also allows, with the same extended release conditions, to reduce the amount of lipophilic substances, with a resulting reduction in the lipid load, corresponding to the absorption of the lipophilic substances used in the body.

Furthermore, the greater uniformity of the mixture allows to reduce mixing and cooling times, with apparent advantages from the production point of view.

An object of the present invention is therefore a process for the preparation of a delayed release solid formulation for oral use comprising the following steps:
a) melting at least one lipid;
b) spraying said at least one melted lipid on at least one active ingredient in the form of a moving powder;
c) cooling the resulting mixture;
d) optional granulation of the mixture;
e) optional compression of the mixture.

In a preferred aspect, the lipid melting step a) is performed at a controlled temperature of between 55 and 80° C., preferably between 60 and 75° C., more preferably between 65 and 70° C.

According to a further preferred aspect, the process according to the present invention is characterized in that the lipid spraying step b) is performed through nozzles arranged linearly with respect to the surface of the active ingredient advancement plane.

Preferably, the number of said nozzles nozzles is greater than 5, and even more preferably the number is between 10 and 60.

In a further preferred aspect, the lipid spraying step b) is performed at a flow rate of 0.005-0.04 l/min per kg of active ingredient, preferably at a flow rate of 0.005-0.015 l/min per kg of active ingredient, more preferably at a flow rate of 0.0075-0.0125 l/min per kg of active ingredient.

Preferably, during the spraying step the temperature of the mixture is maintained at a temperature of between 55 and 60° C.

Preferably, said spraying step is performed a second time while keeping the mixture under stirring and the flow rate at 0.005-0.04 l/min per kg of active ingredient, more preferably at a flow rate of 0.005-0.015 l/min per kg of active ingredient.

According to a preferred aspect of the invention, the lipid spraying step b) is performed through nozzles inclined of 35-55°, preferably of 40-50°, even more preferably of about 45°, with respect to the surface of the active ingredient advancement plane.

According to a further equally preferred aspect of the invention, the nozzles have a diameter of between 0.2 and 4 mm, preferably between 0.4 and 1 mm, more preferably of about 0.6 mm; in addition, they are spaced apart by 0.5-1 cm, preferably by about 1 cm.

According to a further preferred aspect, the orifice of said nozzle is positioned at 10-40 cm from the powder surface, preferably at 15-20 cm from the powder surface. During the lipid spraying step b), the powder advances at a speed of between 0.10 and 0.40 m/sec, preferably at a speed of between 0.15 and 0.35 m/sec.

According to a further aspect of the invention, the active ingredient powder has a particle size of between 50 and 800 μm.

During step c) the mixture, preferably maintained in movement, is cooled to a temperature normally lower than 35° C., preferably of about 30° C. This is done by uniform insufflation of thermoregulated air at temperatures of between 30 and 35° C. Optionally, the mixture is further cooled to a temperature of between 20 and 25° C. Preferably, the air flow rate is of 5-12 cubic meters of air per minute, more preferably of 8-10 cubic meters of air per minute.

In a preferred aspect, the optional granulation of the mixture step d) is performed with a granulator. Preferably, this granulator consists of a mesh screen with 0.8-3 mm, more preferably 1-2 mm holes.

The lipid is preferably a triglyceride, a diglyceride, or a fatty acid, or mixtures thereof; the fatty acid, either in the free form or in the form of a diglyceride or triglyceride, is preferably a fatty acid having a chain of between 8 and 20 carbon atoms, preferably between 14 and 18 carbon atoms, or a mixture thereof; still more preferably, said fatty acid is saturated.

According to a preferred aspect of the invention, said saturated fatty acid is stearic acid; according to a further preferred aspect, said lipid is stearin.

According to an aspect of the present invention, said lipid is present in an amount of between 5 and 60%, preferably between 15 and 35%, more preferably between 20 and 30% by weight, with respect to the weight of the active ingredient.

The active ingredients which may be used in the present invention may be pharmaceutically, nutraceutically, dietetically and/or alimentary active.

The active ingredients with pharmaceutical activity may be selected from non-steroidal anti-inflammatory, tranquilizers, anti-hypertensive and for the control of cholesterol, antihistaminic, antiasthma, anticancer ones.

The active ingredients having dietetic, alimentary and/or nutraceutical activity, optionally also phytotherapic activity, may be included in the following classes: probiotics, mineral salts, tonics, products for the control of cholesterol, multivitamin and multimineral, intestinal function adjuvant, vitamins, venotonics, trophic and adjuvant for joints, products for night-time rest/tranquilizers, cough products, weight control products, liver function adjuvants, antacids, eye health supplements, anti-hair loss products, immune functions adjuvants, products for the urinary tract, memory and cognitive function adjuvant, products for pregnancy and lactation, multifunctional antioxidants, prostate products, throat products, anti-flu drugs, omega 3, products for menopause, peripheral neuropathies adjuvants, products for the treatment of calculosis, such as potassium citrate, other specific supplements.

More specifically, the active ingredients with dietetic, alimentary and/or nutraceutical action may be selected from vitamins, minerals, phytotherapics, and other substances with nutritional and/or physiological effect, such as essential amino acids, branched amino acids, hydroxycaprylic acid (HICA), hyaluronic acid, conjugated linoleic acid (CLA), lipoic acid, nervonic acid, alpha-ketoisocaproate (KIC), arabinogalactan, arabinoxylan, arginine-alpha-ketoglutarate (AAKG), astaxanthin, beta-alanine, betaine, beta-glucans, butyrate, caffeine, carnitine (including L-carnitine), carnosine, chitosan, citicoline, chlorophyll, coenzyme Q10 and ubiquinol, choline, collagen, colostrum, chondroitin sulfate, creatine, dimethylglycine, enzymes (alpha-galactosidase, bromeline, enzymes from fermented maltodextrin, lactase (beta-galactosidase), papain, superoxide dismutase), epigallocatechin gallate, phytosterols, flavonoids (e.g., quercetin, quercitrin, rutin, spireoside, hesperidin, hesperitin, diosm in), phospholipids (phosphatidylcholine, phosphatidylserine, phosphoserine), GABA, gamma oryzanol, glycerophosphoryl-ethanolamine, glycocyamine, glucomannan, glucosamine, glucuronolactone, glutathione, guar gum, hydroxymethylbutyrate, hydroxytyrosol/olive polyphenols, inositol, isoflavones, lactoferrin, lactulose, lycopene, lutein, melatonin, methylsulfonylmethane (MSM), monacolin K from fermented red rice (*Monacus purpureus*), N-acetylcysteine, N-acetyl-D-glucosam ine, NADH, naringin, norvaline, nucleotides, homotaurine, ornithine alpha-ketoglutarate (OKG), palm itoylethanolam ide (PEA), PABA, pectin, pycnogenol, policosanol, polydatin, resveratrol, ribose, S-adenosylmethionine (SAMe), sperm idine, squalene, taurine, theanine, zeaxanthin, meso-zeaxanthin.

The formulation of the present invention may also contain physiologically acceptable excipients; in this case they are normally present in amounts of between 1 and 50% by weight, preferably between 10 and 40%, with respect to the total weight of the formulation.

The physiologically acceptable excipients usable for the formulations according to the present invention may be selected from different classes, such as diluents (compounds added when the mass of the active ingredient is not sufficient for the preparation of the composition); lubricants (which prevent powders from adhering to mechanical parts during the production process); aggregation agents (compounds that increase powders cohesion), disintegrating agents (used to improve tablets disintegration rate); film forming agents (used for capsules and tablets film-coating); dyes (used to improve the aspect of some pharmaceutical forms, for example tablets, or to classify them according to the therapeutic category they belong to, or to distinguish them from other similar products); sweeteners or flavoring agents (added to improve the organoleptic characteristics of the products); antioxidants-antimicrobials (used to extend the product shelf-life).

Excipients are present in an amount of 10-30%, preferably 20-30% by weight, with respect to the total weight of the formulation.

As it will be apparent from the examples, the process according to the present invention allows to obtain a slower release of the active ingredient with respect to the lipid-based delayed release formulations known in the art, such as those described in EP1225876. Furthermore, the process according to the present invention is less exothermic with respect to known processes, specifically with respect to the simple mixing process described in EP1225876.

EXPERIMENTAL SECTION

Description of Usable Equipment
1) Melting Machine for Lipids
It is a stainless steel container, of cylindrical shape with vertical development, having a hemispherical rounded bottom, with a 110 liters gross internal capacity, characterized by the following construction details:

Interspace for direct and uniform heating of the internal surface of the melting machine, consisting of a thermostatic liquid-tight insulating outer jacket, which is filled with a "hydro-glycerin solution", at a defined concentration, able to maintain temperature ranges of between 10° C. and 100° C., depending on the operating conditions required.

Internal surface in AISI 316 stainless steel; at the bottom of the hemispherical rounded bottom part there is a discharge butterfly valve, provided with an automatically adjusting opening, according to the working requirements.

Central shaker with vertical shaft, equipped with horizontal lapping blades, having a specific wing profile, able to mechanically impart, with constant rotary movement, a lamellar stirring to the molten mass, thus favoring uniform transfer and stirring conditions, without turbulence, irregular or whirling motion, for all the particles present in the solution, maintained at regulated and constant temperature values. The rotation speed of the shaker can be automatically adjusted and maintained at values of between 5 and 40 rpm, depending on the different viscosity conditions of the lipids used.

Load sensors, positioned at the base of the melting machine, used both to automatically check and record the amount of solid product loaded, and to automatically adjust the discharge speed of the molten liquid product to be used.

2) Equipment for Transferring and Spraying Lipids
This plant part, for transfer and distribution of the melted lipid product to be sprayed on the moving powder mixture at defined flow rate, temperature and atomization conditions, consists of the following interconnected mechanical components:

Stainless steel, insulated and thermostated rigid piping, having a defined length and calibrated section, with the purpose of ensuring the continuous connection between the melting machine discharge valve, previously described, and the inlet of a thermostated, tight stainless steel chamber, inside which there is a rotary gear pump used to transfer high viscosity oil products.

Forced equalization chamber consisting of a thermostated, cylindrical stainless steel vessel containing, along its horizontal axis, a rigid impeller pump, equipped with six rotating blades, which provide transfer and constant thrust of high viscosity oily products from the inlet to the outlet chamber area. On the circular surface of the equalization chamber, two holes are positioned diametrically opposite to each other; the first to ensure the inlet and the second to ensure the outlet of liquid substances, driven by the rotation of the centrifugal pump. The inlet hole is bigger in size than the outlet hole, in order to ensure a constant and uniform filling of the equalization chamber.

Insulated and thermostated flexible piping, having a defined length and calibrated section, which is connected upstream with the equalization chamber outlet hole and downstream with the supply valve of the perforated spraying cylinder. This connecting pipe is made of flexible material to subsequently place the final dispensing cylinder in different positions on the kneader, according to the process requirements for preparing thermoplastic mixtures.

Final dispensing cylinder consisting of a thermostated, stainless steel rigid hollow tube, provided with an inlet valve for liquids and a series of 20 nozzles, having a diameter of about 0.6 mm, arranged linearly in an ordered sequence along the circular section of the dispensing cylinder. This dispensing device is placed horizontally on the powder kneader in order to spray the liquid lipid on the powder mixture to be kneaded, with an adjustable inclination and flow rate. The number of nozzles, their position and spacing have been calculated to ensure a simultaneous diffused and uniform distribution of a viscous liquid on a surface of powders characterized by different flow rates between the slower inner central part and the more external lateral ones, which have different flowabilities.

FIG. 1 shows a possible embodiment of the lipid transfer and spraying equipment, with the dispensing cylinder placed horizontally on the kneader and the nozzles arranged linearly in an ordered sequence, along the circular section thereof.

3) Kneader

It consists of mechanical equipment equipped with an automatic mixing and kneading system for pulverulent and pasty products, whose construction characteristics are as follows:

Horizontal stainless steel cone shaped container, with 500 liters useful capacity, sectioned along the major axis, placed horizontally with adjustable inclination.

Screw mixer, operated in a counter-current mode, able to ensure uniform mixing conditions for pulverulent or pasty products by means of a central screw, which convey the powder or mixture along the internal surface of the equipment, in counter-current mode, from the lower vertex of the kneader up to the upper base.

The adjustable downward inclination of the vertex of the powder mixing container described above, together with the counter-current movement operated by the screw are able to produce two different cross flow patterns for the powders contained in the kneader, a faster inner one, close to the screw, oriented from the bottom to the top, and the other, the slower return flow, oriented from the top to the bottom along the walls of the mixer.

These two different flowability streams for the powders allow to obtain uniform mixing conditions of the various components in a very short time, which ranges on average from 6' to 10', depending on the particle size and the number and percentage of substances to be mixed.

The central flow, directed from the bottom to the top, close to the screw, conveys the powders with an advancement speed of about 0.3 meters per second, thanks to the thrust provided by the screw; while the peripheral flow, directed from the top to the bottom, makes the powders run along the walls of the kneader at a lower speed, of about 0.2 meters per second, with the same components to be mixed.

Anchoring points of the spraying pipe for melted lipids to be sprayed on the surface of the moving powder, placed on the upper edge of the kneader, to place the spraying pipe at a predetermined distance, depending on the level of the product to be mixed, and to adjust the inclination of the spray nozzles in order to uniformly distribute the melted lipid on the surface of the product to be kneaded and mixed.

The anchoring position of the spraying pipe is placed on the mixer near the upper edge of the kneader, in correspondence to the surface of powders whose movement is slowed due to the crossing flows. Above this position, the spray nozzles are inclined of 45° with respect to the powder surface to uniformly and diffusely distribute the liquid on the pulverulent surface to be kneaded, by directing the nebulized liquid toward a direction opposite to the advancement flow of the powder in the kneader.

FIG. 2 shows the dispensing cylinder, wherein the nozzle inclination angle of 45°, with respect to the active ingredient powder advancement plane, is shown.

Rotating crusher, positioned close to the lower vertex of the kneader; this device is used intermittently during the mixture cooling step, to mechanically break up bulky product agglomerates, which are formed and settled at the vertex of the kneader, which represents the product accumulation point, characterized by reduced flowability and mixing values.

Cooling system for insufflation of refrigerated air, directed towards the surface of the hot mixture at the end of the spraying step. This type of equipment, consisting of a refrigerated insufflator, equipped with a refrigerated air insufflation pipe having a cross section of 20 cm, is used to direct and uniformly distribute a controlled volume of about 6-9 cubic meters per meter of refrigerated air, maintained for a fixed period of time, initially at a temperature of 35-30° C. and subsequently reduced to a value of 25-20° C., on the surface of the mixture maintained in movement. This particular cooling system represents the preferred heat exchange condition to transform the mixture into an amalgamated mass, endowed with new thermoplastic characteristics. At the end of the cooling phase, the mixture is a solid and compact mass, endowed with elastic properties, which allow an easy transformation into a granulate, in which the components in the obtained particles are well amalgamated, resulting in both immediate and extended release values different from those of the initial components.

In the cooling phase, it is important to reach a final temperature of about 30° C. for the amalgamated mixture, in order to be able to granulate it when it is still sufficiently elastic and has not already cured, so as to limit the stress to which the mixture is subjected to be reduced in granules, and its powderyness, while at the same time achieving a better stabilization of the amalgamated particles.

Example 1

1) Lipid Melting

To perform this operation, a 110 liter capacity melting machine was used. For a lipid treatment process for a 200 kg batch of potassium citrate, 40 kg of granular stearin are introduced through the loading mouth of the melting machine. Once the operation is completed, the loading mouth of the melting machine is closed and the product in it is heated, by automatically adjusting the heating temperature of the hydro-glycerin liquid contained in the interspace to a temperature of 67° C.±2° C. When the preset temperature value is reached, the thermoregulation system is maintained at a temperature of 67° C. for a time ranging from 12' to 15'; once this time has elapsed, a visual inspection through the loading mouth is performed to check that the mass, previously collected in the melting machine, is uniformly melted along the inner walls of the melting machine, and that the portion not yet completely melted is free to float and move within the already molten mass.

Once this step is complete, the system automatically starts stirring at a speed of 10 rpm, increasing the temperature of the interspace up to 78° C.±2° C. When this temperature is reached, the thermoregulation system is maintained under 10 rpm constant stirring for a period of 5', at the end of which time the clearness of the obtained solution and the absence of any lumps or product residues not completely melted are visually checked.

2) Product Loading into the Kneader

200 Kg of potassium citrate powder are introduced separately through the loading mouth of the kneader, using a circular sieve equipped with a mesh screen having a 2 mm net gap, in order to separate lumps, foreign bodies, or other solid foreign elements possibly present in the powder to be introduced into the kneader.

Once the loading of the batch to be kneaded is completed, the upper part of the kneader is closed and the spraying cylinder is positioned at a 15 cm distance from the upper edge border, with nozzles inclined of 45° with respect to the surface of the powder to be kneaded. Once the operation is completed, the mixing screw is started, in a counter-current mode, leaving the apparatus inclined with respect to the work plane in the lower position with the vertex pointing downwards.

3) Lipid Addition and Kneading

The melting machine discharge valve is opened, adjusting the flow rate of the spraying system at a rate of 2 l/min, for a duration of 10 minutes, then the liquid addition is stopped. The mass is maintained under stirring for 5 minutes, and the mass temperature is checked to be of between 50° C. e 55° C.

At the end of this step, the remaining part of melted lipid is added to the mixture maintained in movement, still adjusting the flow rate of the spraying system at a rate of 2 l/min, for a duration of 10 minutes; the spray system is then disconnected, and the mixture obtained is maintained under constant stirring for 5 minutes, at the end of which time the mass temperature is checked to be of between 55° C. and 60° C.; if the temperature values are lower than 55° C., stirring of the mixture should be continued until the limit value of 55° C. is reached, in order to stabilize the thermoplastic conditions and to increase the flowability and elasticity of the mixture.

4) Cooling and Final Granulation

At the beginning of this step, thermoregulated air at temperatures of between 35° C. and 30° C. is uniformly insufflated, at a flow rate of between 8 and 10 cubic meters of air per minute, on the surface of the mixture, maintained under constant stirring, for a period of between 12 and 15 minutes. At the end of this time, it is necessary to measure that the mixture has reached a temperature of between 45° C. and 40° C.; if not, cooling with thermoregulated air is continued under the same conditions, while checking every 5 minutes, until a product temperature of less than 45° C. is reached. During the cooling step, a rotating crusher is used for ¾ cycles, each lasting one minute, in order to break up any product agglomerates formed.

Once this first cooling step is completed, further cooling is carried out by insufflation of thermoregulated air at temperatures of between 25° C. and 20° C., at a flow rate of between 6 and 8 cubic meters of air per minute, for a period of between 8 and 10 minutes, at the end of which time it is necessary to measure that the mixture, already previously cooled, has reached a temperature of between 35° C. and 30° C.; if not, cooling with thermoregulated air is continued under the same conditions, while checking every 2 minutes, until a product temperature of less than 35° C. is reached. After completing this phase, once the temperature of 35° C. is reached, the obtained mixture is discharged and granulated by passing it through a horizontal rotating granulator equipped with a mesh screen having a 1.2 mm net gap.

Example 2

Comparison Between a Granulate Obtained by the Method Described in EP1225876 (A) and One Obtained by the Method According to the Present Invention (B).

A. In a double speed SAGA500 screw mixer a coating of the following components is set up:

|  | AMOUNT |
|---|---|
| COATING |  |
| Stearic Acid | 52.5 Kg |
| MIXTURE |  |
| Xylitol | 26.465 Kg |
| Heavy Magnesium Oxide | 87.00 Kg |
| Rice Starch | 1.750 Kg |
| Total | 167.715 Kg |

The stearic acid is melted in steel tanks, each containing about 10 kg. The remaining components are added into the SAGA500 mixer and mixed together for 5 minutes, then the molten stearic acid is added by pouring over the steel tanks containing about 10 kg of stearic acid at a time.

The approximate process duration is of about 15 minutes, from the beginning to the end of the melted stearic acid addition.

Mixture Homogeneity Check.

4 bags (D, E, F, G) of mixture obtained by the process described above are sampled at different points; each of them is granulated on a 1.4 mm braided wire mesh, independently of the others.

Each of the granulates is analyzed, by preparing a 1% by weight aqueous solution and checking the pH of this solution for a total time of 90'. As it can be seen from FIG. 3, the samples thus obtained are not very homogeneous as far as the coating process is concerned, since a solution has a substantially different pH over time compared to the other solutions, and therefore the coating process is not homogeneous and uniform.

B. A mixture having the same qualitative-quantitative composition as described at point A is prepared by using the same equipment described above in the EXPERIMENTAL SECTION.

During the melted stearic acid spraying step, the mixture of the remaining components advances at a speed of 0.15 m/sec. Spraying of stearic acid is carried out at a flow rate of 0.010 l/min per kg of active ingredient.

Then, the mixture is cooled to a temperature below 35° C. by uniform insufflation of thermoregulated air. The approximate process duration is of about 1 hour, from the beginning to the end of the melted stearic acid addition.

4 bags (O, P, Q, R) of mixture are sampled at different points. Each of them is granulated on a 1.4 mm braided wire mesh, independently of the others.

Each of the granulates is analyzed, by preparing a 1% by weight aqueous solution and checking the pH of this solution for a total time of 90'.

As it can be seen from FIG. 4, the obtained samples are more homogeneous compared to those obtained at point A, since the related solutions have substantially the same pH over time, demonstrating a better coating process and homogeneity of the obtained granulate.

The average pH values for the solutions referred to at point A (curve I) and the solutions referred to at point B (curve H) are shown in FIG. 5. As it can easily be seen, curve H, representing a mixture obtained according to the present invention shows, at the same time, lower pH values compared to curve I, representing a mixture obtained according to the method described in EP1225876.

Example 3

Comparison between tablets obtained by the method described in EP1225876 (A) and tablets obtained by the method according to the present invention (B).

A. Coating of potassium citrate monohydrate for tablets with stearic acid by the method described in EP1225876

In a double speed SAGA500 screw mixer, a coating of the following components is set up:

| COATING | AMOUNT |
| --- | --- |
| POTASSIUM CITRATE MONOHYDRATE | 59.5 Kg |
| STEARIC ACID | 8.25 Kg |
| Total | 67.75 Kg |

Stearic acid is melted in steel tanks. Potassium citrate monohydrate is added into SAGA500. The melted stearic acid is then poured over, for a total time of 2 minutes. During the two components mixing step, the temperature is measured at 30-second intervals; the data collected are shown in the table below.

| TEMPERATURE CHECK | |
| --- | --- |
| TIME | MEASURED TEMPERATURE |
| 30 sec | 39° C. |
| 60 sec | 44° C. |
| 90 sec | 48° C. |
| 120 sec | 49° C. |

The mixture thus obtained is then mixed together with the following excipients and then compressed:

| MATERIAL | AMOUNT |
| --- | --- |
| COATED GRANULATE | 67.75 Kg |
| Microcrystalline cellulose | 1.54 Kg |
| Hydroxypropylcellulose | 2.585 Kg |
| Magnesium stearate | 0.29 Kg |
| Silicon dioxide | 0.77 Kg |
| Total | 72.935 Kg |

The compression is carried out by means of a rotary tablet press machine, with the following process parameters, obtaining approximately 52,000 tablets.

| MACHINE TYPE | Rotary tablet press machine |
| --- | --- |
| PUNCH SHAPE | Oval 16.5 × 9 mm |
| WEIGHT | 1.325 g |
| SETTING | |
| Pre-compression thickness (mm) | 6.5 |
| Compression thickness (mm) | 4.2 |
| Dosage (mm) | 11.5 |
| Pre-compression strength, KN (detected) | 33.4 |

B. A mixture having the same qualitative-quantitative composition as that described at point A of the present example is prepared by using the same equipment and the same settings as described at point B of Example 2. Also in this case, the temperature is measured at 30-second intervals; the data detected are shown in the table below.

| COATING TEMPERATURE CHECK | |
| --- | --- |
| TIME | MEASURED TEMPERATURE |
| 30 sec | 31° C. |
| 60 sec | 34° C. |
| 90 sec | 36° C. |
| 120 sec | 38° C. |
| 150 sec | 40° C. |
| 180 sec | 43° C. |
| 210 sec | 45° C. |
| 240 sec | 49° C. |
| 270 sec | 50° C. |
| 300 sec | 49° C. |

As it can be seen, the process according to the present invention is much less exothermic than that described in EP1225876; in fact, the temperature of the mixture increases much more slowly, reaching 49° C. after 300 seconds vs. 120 seconds referred to at point A.

The mixture thus obtained is then used to prepare approximately 52,000 tablets by using the same excipients, the same amounts, the same equipment, and the same operating conditions described at point A of the present example.

The tests carried out to demonstrate the process improvement with respect to the prior art are the elective tests used in the pharmaceutical field according to the (FU European) pharmacopoeia, i.e. disintegration test and dissolution test.

The disintegration test gave the following results:

| TABLETS | Complete disintegration time (minutes) |
|---|---|
| According to the process of the present invention (B) | 225-250 min |
| According to the method described in EP 1225876 (A) | 195-210 min |

As it can be seen, the disintegration time is longer (improved delayed release) in the case of tablets made with the process of the present invention compared to the tablets obtained by the method described in EP1225876.

Dissolution Test

The tablets thus obtained are then subjected to a dissolution test, whose results are shown in FIG. 6. As it can be seen, the active ingredient release takes place more slowly for the tablets obtained from a mixture prepared according to the process of the present invention (B) compared to one obtained according to the method described in EP1225876 (A).

The invention claimed is:

1. Process for the preparation of a delayed release formulation for oral use comprising the following steps:
   a) melting at least one lipid to form a melted lipid, wherein said at least one lipid comprises a lipid comprising a fatty acid;
   b) spraying through a plurality of nozzles said at least one melted lipid on at least one active ingredient in the form of a moving powder, wherein said spaying is performed at a flow rate of 0.005-0.04 l/min per kg of active ingredient by nozzles arranged linearly with respect to a surface of the active ingredient advancement plane to form a resulting mixture;
   c) cooling the resulting mixture.

2. Process according to claim 1, characterized in that the lipid melting step a) is performed at a temperature of between 55 and 80° C.

3. Process according to claim 1, characterized in that the number of said nozzles is greater than 5.

4. Process according to claim 1, characterized in that the lipid spraying step b) is performed through nozzles inclined of 35°-55°.

5. Process according to claim 1, characterized in that said nozzles have a diameter of between 0.2 and 4 mm.

6. Process according to claim 1, characterized in that said nozzles are spaced apart by 0.5-1 cm.

7. Process according to claim 1, characterized in that the orifices of said nozzles are positioned at 10-40 cm from the powder surface.

8. Process according to claim 1, characterized in that the powder advances at a speed of between 0.10 and 0.40 m/sec.

9. Process according to claim 1, characterized in that said at least one active ingredient in the form of a powder has a particle size of between 50 and 800 µm.

10. Process according to claim 1, characterized in that during step c) the mixture is cooled to a temperature lower than 35° C.

11. Process according to claim 10, characterized in that the cooling is performed by insufflation of air at a temperature of between 30 and 35° C.

12. Process according to claim 1, characterized in that said at least one lipid further comprises a triglyceride, a diglyceride, or a mixture thereof.

13. Process according to claim 1, characterized in that the fatty acid has a chain length of between 8 and 20 carbon atoms.

14. Process according to claim 1, characterized in that said fatty acid is saturated.

15. Process according to claim 1, characterized in that said at least one active ingredient is pharmaceutically, nutraceutically, dietetically and/or alimentary active.

16. Process according to claim 1, characterized in that said lipid is present in an amount of between 5 and 60% by weight.

17. Process according to claim 1, characterized in that said at least one active ingredient is mixed with at least one physiologically acceptable excipient.

18. Process according to claim 1, characterized in that said fatty acid comprises stearic acid.

* * * * *